United States Patent [19]

Lihme et al.

[11] Patent Number: 5,780,593
[45] Date of Patent: Jul. 14, 1998

[54] METHOD OF ISOLATING BIOMOLECULES BY ION EXCHANGE

[75] Inventors: Allan Otto Fog Lihme, Birkerød; Margit Irene Aagesen, Copenhagen Ø; Claus Gammelgård-Larsen, Skanderborg; Katrine Hvid Ellegård, Århus N, all of Denmark

[73] Assignees: Kem-En-Tec A/S, Copenhagen O; Md Foods AMBA, Viby J, both of Denmark

[21] Appl. No.: 403,807

[22] PCT Filed: Sep. 17, 1993

[86] PCT No.: PCT/DK93/00299

§ 371 Date: Jul. 12, 1995

§ 102(e) Date: Jul. 12, 1995

[87] PCT Pub. No.: WO94/06822

PCT Pub. Date: Mar. 31, 1994

[30] Foreign Application Priority Data

Sep. 17, 1992 [DK] Denmark ................... 1143/92

[51] Int. Cl.[6] ............... C07K 16/00; B01D 15/08
[52] U.S. Cl. ............ 530/361; 530/362; 530/363; 530/366; 530/385; 530/386; 530/390.5; 530/416; 530/427; 210/198.2; 210/635; 210/656; 210/660
[58] Field of Search ............... 530/361, 362, 530/363, 366, 385, 386, 390.5, 416, 427; 210/198.21, 635, 656, 660

[56] References Cited

U.S. PATENT DOCUMENTS

| | | | |
|---|---|---|---|
| 4,358,465 | 11/1982 | Brule et al. | 426/42 |
| 4,495,176 | 1/1985 | Brule et al. | 524/128 |
| 4,876,398 | 10/1989 | Lin et al. | 568/804 |
| 5,112,949 | 5/1992 | Vukovich | 530/380 |
| 5,466,368 | 11/1995 | Arvidsson et al. | 210/198.2 |

FOREIGN PATENT DOCUMENTS

| | | |
|---|---|---|
| 0 090 406 A1 | 10/1983 | European Pat. Off. |
| 0 239 565 A2 | 9/1987 | European Pat. Off. |
| 0 476 199 A1 | 3/1992 | European Pat. Off. |
| 0476199 | 3/1992 | European Pat. Off. |
| WO 92/18526 | 10/1992 | WIPO |

OTHER PUBLICATIONS

Juillerat et al, *Journal of Dairy Research*, vol. 56, pp. 603–611, 1989.

"The Separation and Amino Acid Composition of a Pure Phosphopeptone Prepared from B–Casein by the Action of Trypsin[2]", R.F. Peterson et al., Amino Acid Composition of a Pure Phosphopeptone, Jan. 5, 1958, vol. 80, pp. 95–99.

"Séparation chromatographique de peptides issus de 1 'hydrolyse enzymatique de protéines de lactosérum et de caséines", Frederique Touraine et al., Le Lait, 1987, 67 (4), 419–435 (Summary in English).

"Tryptic phosphopeptides from whole casein", Marcel A. Juillerat et al., Journal of Dairy Research (1980) 56, 603–611.

"Glutamine purification –from Corynebacterium sp. fermentation broth by cation exchange chromatography, anion exchange chromatography and precipitation", & KR 8912915, 890907, Dialog Information Services, File 357, Biotechnology abstracts, Dialog acc. No. 142332 (Miwon–Foods).

*Primary Examiner*—Douglas W. Robinson
*Assistant Examiner*—Abdel A. Mohamed
*Attorney, Agent, or Firm*—Finnegan, Henderson, Farabow, Garrett & Dunner, L.L.P.

[57] ABSTRACT

A method of isolating a biomolecule from a medium containing biomolecules by ion exchange wherein the ion exchange material consists of a material having ion exchanging groups which can be transformed from a charged form to an uncharged form; the eluant comprises a charge neutralizing acid or base transforming the ion exchanging groups from the charged form to the uncharged form; and the charge neutralizing acid or base has a concentration in the eluant which is twice, preferably equal to or less than the concentration of the ion exchanging groups of the ion exchange material; the ion exchange material being in a packed, hydrated state. Preferably the method is for the isolation of phosphopeptides from a medium containing casein hydrolysates and the use of such isolated biomolecules is for the production of a food, a feed, a health care product, a cosmetic, or a pharmaceutical.

35 Claims, 5 Drawing Sheets

METHOD OF ISOLATING BIOMOLECULES BY ION EXCHANGE

BACKGROUND OF THE INVENTION

This invention relates to a method of isolating a biomolecule such as a protein or peptide from a medium containing biomolecules by ion exchange; a method of isolating phosphopeptides from casein hydrolysates; and the use of a biomolecule isolated according to such methods in the production of a food, a feed, a health care product, a cosmetic, or a pharmaceutical.

1. The Technical Field

Isolation or fractionation of biomolecules in a medium containing biomolecules by ion exchange usually involves the binding of the biomolecule to an ion exchanger at an appropriate pH and low salt concentration e.g. less than 0.1M salt of the medium. Following wash out of unbound components, the bound biomolecules are eventually eluted by a suitable eluant.

In general, elution of biomolecules bound to the ion exchanger may be achieved by changing the pH and/or increasing the salt concentration of the medium whereby the equilibrium reaction of bound/unbound biomolecules is shifted to unbound biomolecules. Especially for proteins and peptides to be used in food, feed, health care, cosmetic, or pharmaceutical products, it is of great importance that the biomolecules are eluted from the ion exchanger under conditions which minimize the destruction of their biological and physico-chemical properties. At the same time, it is highly desirable to keep a low salt concentration in the eluate whereby desalination of the eluate, losses of the isolated biomolecule and increased costs of the final product can be avoided.

Biomolecules of interest include as mentioned proteins and peptides, particularly casein phosphopeptides which have attracted increasing attention as important biological molecules due to their calcium binding properties.

2. Prior Art Disclosure

European Patent Application No. 0 476 199 discloses a method of separating phosphopeptides from an aqueous medium containing casein hydrolysates wherein the pH of the medium is adjusted to 4.6 and the solids therefrom are separated; the pH of the medium is adjusted to a value larger than 4.0, preferably larger than 6.0; the medium is subjected to ion exchange, thereby saturating the resin, and the unbound material is collected; the bound phosphopeptides are eluted from the ion exchange resin with a suitable eluant; and the obtained product is dried.

The preferred ion exchanger resin is an anion exchanger. As a suitable eluant there is suggested an aqueous medium having a pH less than 4.0, or an aqueous medium having a pH larger than 4.0 and a salt concentration larger than 100 mM, preferably 500 mM; said salt exemplified by sodium chloride. As an example of an eluant having a pH less than 4.0, an aqueous medium having a pH of 1.0 is given. However, no indication is provided about the substance used to obtain said pH. After elution the eluate is adjusted to pH 7.0 and subsequently dried.

Thus, eluting the anion exchange resin is either performed with an acidic eluant, which provides a low pH in the eluate, or eluting the anion exchanger with a neutral or basic eluant also containing high concentrations of salt, which provides too much salt in the eluate.

A major drawback of this method is the high contents of salt in the final product. In the case that hydrochloric acid is used to achieve a pH of 1.0 in the eluant, the subsequent neutralization to pH 7.0 with sodium hydroxide results in a sodium chloride concentration of at least 0.1M in the eluated aqueous medium before the drying step. As such aqueous eluates rarely contains more than a few percent of product, drying of the eluate will result in an unacceptable high contents of salt in the dried product. Alternatively the eluate may be desalinated before drying but this decreases the yield of separated phosphopeptides and increases the costs of the final product. Furthermore, the use of low pH for elution may generally lead to partial destruction of the biological and physico-chemical properties of the eluted proteins and peptides.

Juillerat et al., Journal of Dairy Research, Vol. 56, 603–611 (1989), discloses a procedure for producing phosphopeptides from sodium caseinate comprising salt gradient elution of a demineralized peptide solution loaded on a strong anion exchange resin (QAE-Sephadex A25) at pH 4.5 by stepwise elution with 0.1M, 0.2M, and 0.5M KCl followed by demineralization of the pooled fractions. As the phosphopeptides elute from the anion exchange resin with the eluant 0.5M KCl, a disadvantage of this method is the large amount of salt in the eluate which requires a desalination treatment of the eluate before it can be used in a final product.

European Patent Application No. 0 090 406 discloses a method of producing phosphopeptides from sodium caseinate comprising hydrolysis with crystalline trypsin; elimination of unreacted casein and impurities by precipitation of the hydrolysis mixture at a pH of 4.5–5.0 followed by centrifugation; and addition of a metal ion such as barium, calcium, iron or magnesium and, if necessary, a hydrophilic solvent such as methanol, ethanol, propanol, butanol and acetone to precipitate and recover the phosphopeptide. It is indicated that casein phosphopeptide may be produced by ion-exchange chromatography, but no specific procedure is disclosed. Also, a chromatographic procedure for removal of bitter tasting peptides from the hydrolysate solution is disclosed. A disadvantage of this method is the use of organic solvents. Another disadvantage is the low purity obtained.

U. S. Pat. Nos. 4,358,465, 4,495,176 and 4,816,398 disclose a method of recovering phosphopeptides from a casein-based material comprising enzymatic hydrolysis of the material; ultrafiltrating the resultant hydrolyzate to obtain a permeate containing phosphopeptides and non-phosphorylated peptides; adding a bivalent cation salt to form aggregates of the phosphopeptides; and ultrafiltrating the aggregates of phosphopeptides allowing non-phosphorylated peptides to pass through, and the retained phosphopeptides to be recovered. A disadvantage of this method is the low purity obtained.

International Application WO92/18526 also discloses a method of preparing selected phosphopeptides, particularly anticariogenic phosphopeptides, from casein using ultrafiltration.

F. Touraine et al., Le Lait, Vol. 67, 419–436, 1987, disclose chromatographic fractionation of peptides from whey and casein. The fractionation is performed on a DEAE-anion exchanger whereto the peptides are bound and subsequently eluted by 0.1M hydrochloric acid. This elution procedure has the disadvantage of providing a low pH in the eluate. There is no indication or suggestion of the use of a base for elution of the anion exchanger.

R. F. Peterson et al., J. Am. Chem. Soc., Vol. 80, pp. 95–99, 1958, disclose fractionation of casein-peptides originating from only β-casein on a Dowex 50×2 (strongly acidic cation exchanger). The phosphopeptides were bound to the strongly acidic cation exchanger at a pH below 3.0 and could be eluted with 0.1 ionic strength ammonium formate at pH 3.4. This procedure provides a high concentration of ammonium formate in the eluate, which has to be eliminated by sublimation and an extra ion-exchange step. There is no indication or suggestion of the binding of phosphopeptides to a weakly acidic cation exchanger or a weakly basic anion exchanger.

DISCLOSURE OF THE INVENTION

OBJECT OF THE INVENTION

It is the object of the present invention to provide a method of isolating a biomolecule such as a protein and peptide from a medium containing biomolecules by ion exchange whereby it is obtained that the eluate contains a low salt concentration so that a desalination treatment of the eluate can be avoided. Further, it is the object of the present invention to provide such a method wherein the pH of the eluate is within an acceptable range which does not require any additional pH adjustment to accommodate the eluate to subsequent applications of the isolated biomolecule, and which does not harmfully affect the biological and physico-chemical properties of the eluted biomolecule.

Still further, it is the object of the present invention to provide such a method wherein the constituents of the eluant are acceptable in food, feed, health care products, cosmetics, and pharmaceuticals.

Also, it is the object of the present invention to provide such a method which results in a high yield and a high purity of the isolated biomolecule.

Especially, in the isolation of phosphopeptides from a medium containing casein hydrolysates, it is the object of the present invention to provide such a method which simultaneously removes the bitter tasting peptides.

SOLUTION ACCORDING TO THE INVENTION

According to the invention, these objects are fulfilled by providing a method of isolating a biomolecule from a medium containing biomolecules by ion exhange comprising the steps defined in the introductory part of claim 1 and characterized by the features of the characterizing part of claim 1.

The ion exchange material consists of a material having ion exchanging groups which can be transformed from a charged form to an uncharged form whereby it is ensured that the ion exchanger can be neutralized so that the bound molecule can be unbound.

According to the invention, the eluant comprises a charge neutralizing acid or base transforming the ion exchanging groups from the charged form to the uncharged form whereby it is ensured that neutralization of the ion exchanger is obtained by the eluant.

Further, the charge neutralizing acid or base has a concentration in the eluant which is up to twice, preferably equal to or less than the concentration of the ion exchanging groups of the ion exchange material; said ion exchange material being in a packed, hydrated state whereby it is ensured that the biomolecules are eluted into an eluate exhibiting a low salt concentration which cannot exceed a concentration corresponding to the concentration of charge neutralizing acid or base in the incoming eluant, that adjustment of pH is not required, and that the eluted biomolecules are exposed to harmless pH values;

said low concentration of the charge neutralizing acid or base in the eluant presumably causing the titration of the charged ion exchanging groups in the zone of the eluted molecules to be rather flat.

Based on extensive laboratory experiments, it surprisingly turned out that biomolecules such as proteins and peptides may be eluted from ion exchange resins without the use of high salt concentrations and without providing an extreme pH-value in the eluate.

Thus, it was observed that ion exchangers of the weak type e.g. non-quarternary amine based anion exchangers such as diethylaminoethyl (DEAE)-based ion exchangers and carboxylic acid based cation exchangers can be eluted so that the neutralization of the ion exchanging (charged) groups on the ion exchange resin provide an uncharged resin.

Further, it was observed that a gradual neutralization of the charged ion exchanging groups functioning as a buffer substance ensured that the bound and released biomolecule was kept in a medium having a low salt content and non-extreme pH-values which were acceptable to the eluted biomolecules.

This gradual neutralization is against the general teaching of ion exchange chromatography, e.g. see "Ion Exchange Chromatography—Principles and Methods", PHARMACIA FINE CHEMICALS, Uppsala, Sweden, March 1980, where anion exchangers are taught to be eluted with a decreasing pH gradient and cation exchangers are taught to be eluted with an increasing pH gradient.

Further, this ensures that no buffer substances are required in the eluant, because the buffering effect is associated with the ion exchanging groups of the ion exchanger.

In the case of weakly acidic ion exchangers such as carboxylic acid containing ion exchangers, this effect is surprisingly achieved by eluting with a dilute aqueous solution of an acid, or in the case of weakly basic ion exchangers such as DEAE-based ion exchangers by eluting with a dilute aqueous solution of a base.

ADVANTAGEOUS EFFECTS AND PREFERRED EMBODIMENTS

According to the invention, the ion exchange material consists of a material having ion exchanging groups which can be transformed from a charged form to an uncharged form. Suitable ion exchange materials include both anion and cation exchanging materials known in the art having a sufficient ion exchange capacity.

In a preferred embodiment, the concentration of the ion exchanging groups of the ion exchange material is in the range from about 50 to about 500, preferably from about 100 to about 300, particularly from about 150 to about 250 microequivalents per milliliter packed, hydrated ion exchange material.

According to the invention, the eluant comprises a charge neutralizing acid or base transforming the ion exchanging groups from the charged form to the an uncharged form. Suitable charge neutralizing acids or bases include both strong and weak bases, known in the art having a suitable $pK_a$ or $pK_b$ less than that of the ion exchange material, whereby the equilibrium of the ion exchanging groups is shifted from the charged form to the uncharged form.

For example an anion exchanger based on amino exchanging groups, e.g. DEAE-groups, requires an eluant having a base strength comparable with or larger than the base strength of the amino groups on the anion exchanger. Particularly a considerably stronger base strength, e.g. more than one $pK_b$, is preferred.

Preferred bases include sodium hydroxide, potassium hydroxide, calcium hydroxide, sodium carbonate, potassium carbonate, tertiary phosphates and ammonium hydroxide. A particularly preferred base is sodium hydroxide.

Similar consideration applies for cation exchangers where the particularly preferred acids include hydrochloric acid, citric acid, sulphuric acid and phosphoric acid.

In a preferred embodiment, the ion exchange material is an anion exchanger, and the charge neutralizing acid or base is a base having a $pK_b$ less than the $pK_b$ of the anion exchanger, preferably more than 2 $pK_b$ units less, most preferred a $pK_b$ less than 1.

In another preferred embodiment, the ion exchange material is an cation exchanger, and the charge neutralizing acid or base is an acid having a $pK_a$ less than the $pK_a$ of the cation exchanger, preferably more than 2 $pK_a$ units less, most preferred a $pK_a$ less than 1.

Generally, the preferred acids and bases are relatively strong. Therefore, relatively extreme pH-values are obtained. Thus, 0.1M sodium hydroxide provides a pH of 13, and 0.1M hydrochloric acid provides a pH of 1. However, it has been observed that when using such acids and bases in the suggested concentrations for elutions of the respective ion exchangers, the pH of the eluate is within acceptable limits, e.g. between pH 3 and pH 10, resulting in an eluate near pH 7. Furthermore, it has been observed that the inorganic salt concentration is low in the eluate containing the isolated molecule, i.e. the salt concentration is lower than the salt concentration of the eluant.

According to the invention, the charge neutralizing acid or base has a concentration in the eluant which is twice, preferably equal to or less than the concentration of the ion exchanging groups of the ion exchange material; said ion exchange material being in a packed, hydrated state.

In a preferred embodiment the concentration of the charge neutralizing acid or base in the eluant is in the range from about 0.1% to 200%, generally from about 1% to 100%, particularly from about 5% to about 75%, preferably from about 5 to about 50%, most preferred from about 5% to about 35% of the concentration of the ion exchanging groups of the packed, hydrated ion exchange material.

Generally, the constituents of the eluant are selected to be acceptable for the later use of the eluate or product, i.e it is avoided to apply components such as buffers which have to be removed from the eluate.

The medium containing biomolecules is applied to the optionally equilibrated ion exchange material by any method known in the art. It is however preferred that all of the biomolecules to be isolated have been exchanged with the ion exhchanging groups. For example, it is preferred that almost all chloride ions of an anion exchanger have been exchanged with the phospopeptides to be isolated whereby they only contributes very little to the total salt in the eluate.

Binding of the biomolecule to be isolated to the optionally equilibrated ion exchange material can be ensured by any method known in the art. Thus, the selection of suitable acids or bases, pH, salt, and salt concentration of the eluant and of the optionally applied washing solution allow the person skilled of the art to control the biomolecules to be bound to the ion exchange material, and the amounts thereof, and to control the unbound molecules or contaminants to be washed out.

In a preferred embodiment, a salt preferably NaCl having a concentration in the range from about 0.1 normal to about 0.3 normal is added to the medium containing biomolecules prior to the step of applying the medium to the equilibrated ion exchange material, to the washing solution during the washing step, to both or to none.

Generally, any biomolecule which can exchange with an ion exhanging group can be isolated according to the invention.

In a preferred embodiment, the biomolecule is selected from proteins or peptides contained in biological)materials such as food, feed, biproducts or waste produced in the production of foods and feeds.

Particularly, the biomolecule is a protein selected among enzymes; albumin, hemoglobin, and immunoglobulin, particularly from human porcine or bovine blood; milk proteins such as immunoglobulin, lactoforrin, lactoglobulin, and lactoperoxidase from milk or whey; and egg white proteins; or the biomolecule is a peptide, or a group of peptides such as phosphopeptides, particularly phosphopeptides from casein.

The ion exchange may be carried out by any method known to in the art. However, in order to avoid the problems of clogging and rise of pressure over the column by ion exchange of large volumes, it is an advantage that the process wholly or partially is caried out in a fluidized bed, and that the application of the medium containing biomolecules, the washing out of unbound biomolecules, or both, are carried out in a batch process.

According to a preferred embodiments, the method is carried out, wholly or partially in a fluidized bed; and the application of the medium containing biomolecules, the washing out of unbound biomolecules, or both, are carried out in a batch process.

It is particularly preferred that the ion exchange material is an ion exchanging density controlled particle prepared according to the teaching of the International Application WO 92/00799 the content of which is hereby incorporated by reference.

Isolation of Phosphopeptides

In a particular aspect of the invention, there is provided a method of isolating phosphopeptides from a medium containing casein hydrolysates wherein the medium is treated with an ion exchanger binding the phosphopeptides; optionally the unbound components are washed out; and the bound phosphopeptides are eluted with an eluant; said method characterized in a) that the ion exchanger is an anion exchanger, preferably an amine based anion exchanger having a $pk_b$ in the range from about 3 to about 10, preferably from about 4 to about 9;

b) that the eluant is an aqueous solution of a base having a pH larger than 4 without added salt, preferably a diluted aqueous solution of a base having a $pK_b$ value less than 5, preferably less than 3, most preferred less than 1; and c) preferably the base has a concentration less than 0.4N, preferably less than 0.2N, more preferably less than 0.1N, most preferred 0.05N or less, whereby it is obtained that the eluate has a low salt concentration and a harmless pH to the phosphopeptides. This effect cannot be obtained by prior art methods.

In a preferred embodiment, the medium, the washing solution, or both, are added salt preferably 0 to 0.1M sodium chloride, whereby undesired binding of other components than phosphopeptides is avoided.

Salts not added to the eluant or salt added to the medium, the washing solution, or both, are usual salts defined as the reaction product of an acid and a base such as sodium chloride.

In other preferred embodiments, the medium has a pH in the range from about 3.5 to about 5.0 and contains about 0.1M sodium chloride; or the washing solution contains about 0.1M sodium chloride, whereby a strong binding of the phosphopeptides is obtained and an undesired binding of the other components is avoided.

In still another embodiment, the base is sodium hydroxide or ammonium hydroxide.

In another particular aspect of the invention, there is provided a use of a biomolecule isolated according to the invention for the production of a food, a feed, a health, care product, a cosmetic, or a pharmaceutical.

Especially there is provided a use of casein phosphopeptides isolated according to the invention from hydrolyzed casein/caseinates hydrolyzed with a proteinase such as trypsin, particularly the use of such casein phosphopeptides as additives in health foods and drinks, such as casein phosphopeptide enriched milk for increasing the in vivo absorption of calcium, e.g. for the prevention of osteoporosis.

Preferably, the unbound components washed out are collected for further use, e.g. as a growth substrate for bacterial growth.

Definition of Expressions

Within the present context the expression "phosphopeptide" designates a phosphorylated peptide in form of a conjugated peptide in which the non-peptide portion is a residue of phosphoric acid. In particular the expression "casein phosphopeptide" or "CPP" designates a phosphopeptide containing a casein fragment. The expression "dephosphorylation" designates the removal of one or more phosphoryl groups.

The expressions "ion exchanger of the weak type" or a "weak ion exchanger" are intended to designate an ion exchanger which is not completely ionized over a wide pH range. Thus, the degree of dissociation and consequently the ion exchange capacity of the weak ion exchanger varies much more markedly with pH than for a "strong ion exchanger" which is completely ionized.

The expression "diafiltrate" designates the soluble part of a solution which has passed through an ultrafiltration membrane.

DETAILED DESCRIPTION

Ion Exchange Using A Weak Ion Exchanger

Figure 1A:
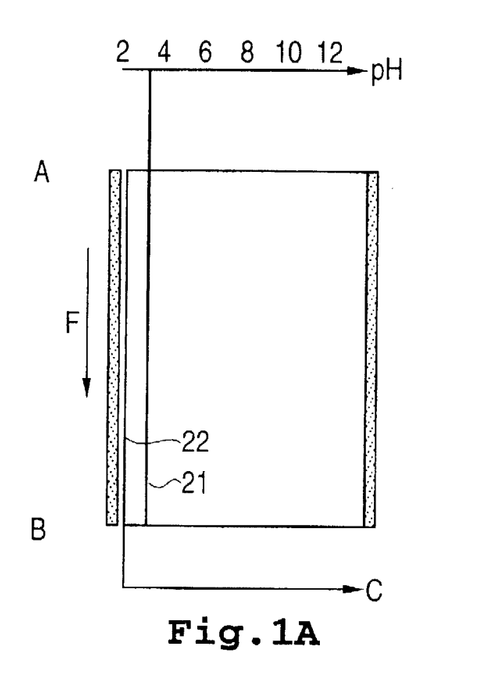
FIGS. 1A–1C show sketches of ion exchange columns containing a weak ion exchanger to which biomolecules have been loaded at top (1A) and eluted with a low (1C) and a high (1B) concentration of base in the eluant.
Figure 1B:
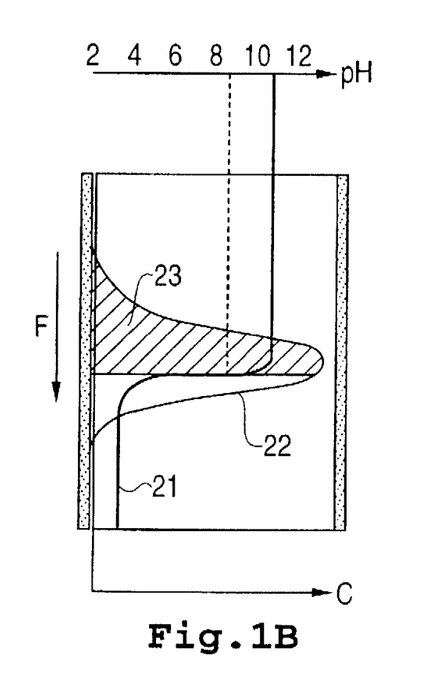
Figure 1C:
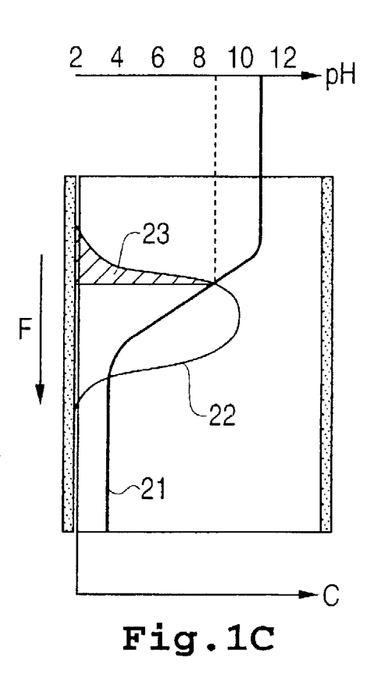

Referring to Figs. 1A–C sketches are shown of ion exchange columns containing a weak ion exchanger (anion exchanger) to which biomolecules have been loaded.

In FIG. 1A biomolecules have been loaded at the top, A, on to the column at a pH about 4, whereafter unbound biomolecules are washed out (in the direction of the arrow, F) at this pH through the bottom, B. The pH of the mobile phase is about 4 as indicated by the curve 21, and the concentration of unbound biomolecules is zero as indicated by the curve 22.

In FIG. 1B the bound biomolecules are eluted (in the direction of the arrow, F) by means of an eluant containing a charge neutralizing acid or base (here a base) having a concentration which is much larger than the concentration of the ion exchanging groups of the ion exchange material. As the eluant moves down, the ion exchanging groups are immediately neutralized by reaction with the base and the bound biomolecules become unbound biomolecules as indicated by the curve 22. Due to the excess of the charge neutralizing base, the pH of the mobile phase rises very rapidly to an extreme pH value as indicated by the curve 21. Under these conditions a major fraction of the unbound biomolecules is exposed to an environment of extreme pH, e.g. the fraction of biomolecules under the elution peak indicated by the area 23 is exposed to a pH above 10.

A similar situation exists for ion exchange using a weak cation exchanger, wherein the eluant contains a charge neutralizing acid having a concentration which is much larger than the concentration of the ion exchanging group of the ion exchanger. In this case the major fraction of the unbound biomolecules are exposed to low pH.

In either case the exposure of the biomolecule to extreme pH values may damage their biological and physicochemical properties.

This problem can be avoided by elution by means of an eluant containing a charge neutralizing acid or base (here a base) having a concentration according to the invention which is twice, preferably equal to or less than the concentration of the ion exchanging groups of the ion exchange material.

In FIG. 1C the bound biomolecules are eluted (in the direction of the arrow, F). As the eluant moves down, the ion exchanging groups of the ion exchanging material are gradually neutralized and the excess of the charge neutralizing base is gradually increased, resulting in a pH of the mobile phase gradually rising to an extreme pH value as indicated by the curve 21.

The biomolecule is eluted in a slightly-larger volume of an environment having acceptable pH values, i.e. only a small fraction of the unbound biomolecules in the elution peak indicated by the area 23 is exposed to a pH above 10.

Isolation of Phosphopeptides

Figure 2:
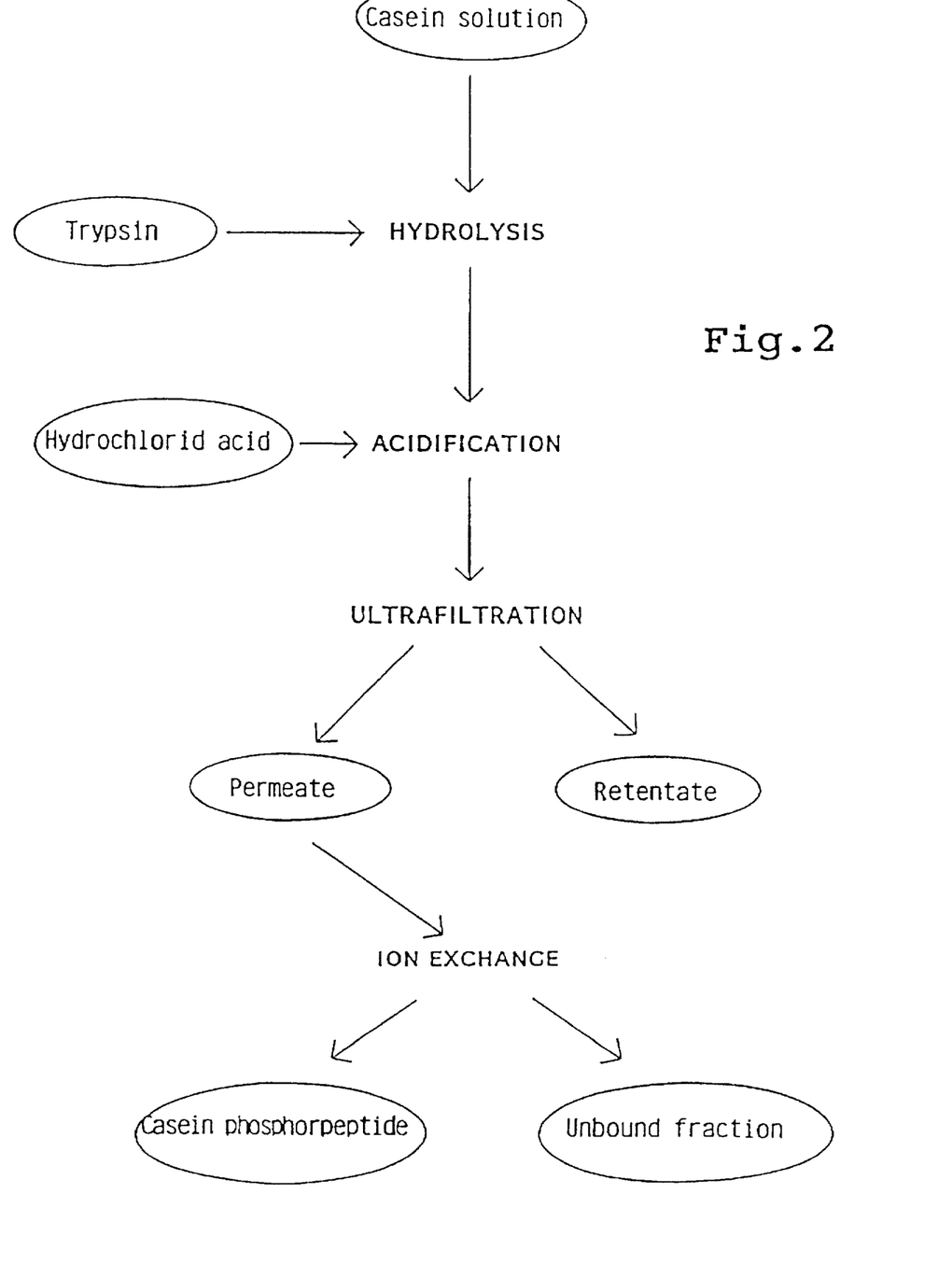
FIG. 2 shows a flow chart of the total process of isolating phosphopeptides from a casein solution wherein the permeate of the ultrafiltration step is subjected to ion exchange according to the invention.

Referring to FIG. 2 there is shown a flow chart of a method of isolating phosphopeptides from a casein solution wherein the permeate obtained in the ultrafiltration step is subjected to an ion exchange treatment according to the invention to isolate casein phosphopeptides.

The first step in the method consists in providing a solution containing casein (casein-solution). As starting material for production of casein phosphopeptides any caseinate can be used, e.g. any casein in conjunction with any mono or divalent cation such as sodium, calcium or potassium.

The second step consists in the hydrolysis of the solubilized caseinate. This can be done by any method known in the art. Preferably, the solubilized caseinate is hydrolyzed by treatment with a suitable proteinase, preferably hydrolysis with trypsin (PTN 3.0. Type Special, Novo Nordisk, Denmark) for two hours at pH 8.0.

The third step consists in the acidification of the hydrolysate for the production of a precipitate. This can be done by any method known in the art. Preferably, the pH of the hydrolysate is decreased (acidified) by addition of a suitable acid known in the art, preferably hydrochloric acid.

The fourth step consists in ultrafiltration of the acidified hydrolysate. This can be done by any method known in the art. Particularly, the precipitate is isolated from the soluble peptides by ultrafiltration, preferably by use of CP 60 PP membranes mounted in a DDSmodule, APV Pasilac A/S, Denmark, after one hour of flocculation.

The fifth step consists in ion exchange of the soluble peptides retained in the permeate from the ultrafiltration step, wherein casein phosphopeptides are isolated from the unbound fraction of impurities, such as non-phosphorylated peptides and other unbound solutes according to the invention.

Test of Purity

For the evaluation of purity of isolated samples containing casein phosphopeptides and/or samples containing the corresponding dephosphorylated peptides analytical ion exchange chromatography was performed according to the fast protein liquid chromatographic (FPLC) procedure on Mono Q resin described by Jullerat et al., Journal of Dairy Research Vol. 56, 603–611, 1989, the content of which is hereby incorporated by reference.

Fast liquid protein chromatography (FPLC) equipment, Mono Q HR 5/5 column, and Variable Wavelength Monitor was supplied by Pharmacia LKB, Sweden.

Reagents comprise Buffer A: 0.02M Tris/HCl, pH 8.0 and Buffer B: 0.02M Tris/HCl, 1M NaCl, pH 8.0 prepared from tris(hydroxymethyl)aminomethane, $C_4H_{11}NO_3$, Tris; sodium chloride, NaCl; hydrochloric acid, HCl; and deionized water.

Alkaline phosphatase from calf intestine was of grade I supplied by Boehringer Mannheim, Germany.

"FPLC Mono Q Resin Procedure"

Samples of 0.5 mg dry solid/run were loaded at 5 min and the phosphopeptides or dephosphorylated peptides were eluted by a 60 min linear gradient from 0% to 50% buffer B from 8 to 68 min followed by 3.5 min of 100% buffer B and 12 min of buffer A. Elution of peptides was monitored by measuring their absorbance at 214 nm.

"Dephosphorylation of Phosphopeptides"

Dry solid samples containing phosphopeptides were dissolved in deionized water to obtain a 10 (w/v)% aqueous solution which was diluted 1:3 in buffer A. 200 µl of this solution was treated with 25 µg of alkaline phosphatase for one hour at 37° C. followed by inhibition of the enzyme by heating the sample to 100° C. for 1 min.

The reaction mixture was further diluted 1:3 prior to submission for test of purity by the FPLC procedure in which 45 µl of the diluted reaction mixture was injected onto the Mono Q column.

"Shift of Elution Times for Dephosphorylated Phosphopeptides"

The Mono Q bound peptides were eluted during the 60 min sodium chloride gradient according to their increasing negative surface charge. The highly negative phosphopeptides eluted after approximately 30 min of gradient, at 38 min in the chromatograms, corresponding to approximately 0.23M NaCl whereas the identical but dephosphorylated peptides eluted before 30 min of gradient.

The reason for this shift in elution times of the dephosphorylated phosphopeptides is that the dephosphorylation of each peptide results in a considerable decrease in the negative surface charge, so that the dephosphorylated phosphopeptides are less strongly bound to the ion exchanger than the phosphopeptides.

Comparison of chromatograms of samples containing phosphopeptides and dephosphorylated phosphopeptides would indicate whether all peptides were phosphorylated or not. Therefore, the presence of impurites such as non-phosphorylated peptides would be indicated by one or more non-shifted peaks in the chromatograms, for which the net negative charge of the corresponding peptide has not been changed by the dephosphorylation reaction.

"Results"

Studies of casein phosphopeptides isolated according to the Invention have shown that all isolated phosphopeptides have lost negative charge following dephosphorylation which indicates that the isolated phosphopeptides consists of only phosphopeptides.

The product is 100% pure phosphopeptides as opposed to the prior art products which only contain approximately 67% pure phosphopeptides.

Also, the absence of hydrophobic peptides in the isolated phosphopeptides indicates the absence of bitter tasting peptides. Consequently, bitter tasting peptides are not transferred to the product, which is verified by tasting the isolatd phosphopeptides.

EXAMPLES

Example 1
Isolation of Casein Phosphopeptides Using An Amine Based Weak Anion Exchanger A chromatography column with an internal diameter of 1.6 cm was packed with a slurry of 12 ml DEAE-Sepharose Cl 6B (Pharmacia, Sweden) having 130–170 micromoles aminogroups per milliliter and exhibiting a $pK_b$ in the range from 4 to 10. The column was first washed with 20 ml 1M hydrochloric acid followed by 120 ml 0.1M sodium chloride.

A 10% solution of sodium caseinate was hydrolyzed with trypsin. The insoluble fraction was removed by adjustment of the pH to 4.6 followed by ultrafiltration.

The obtained solution containing the casein phosphopeptides was diluted with one volume 0.2M sodium chloride to obtain a final salt concentration of 0.1M.

40 ml of this solution was applied to the DEAE-Sepharose column. The unbound fraction was washed out with a solution of 0.1M sodium chloride.

Elution of the bound phosphopeptides was performed by application of a solution of 0.05M sodium hydroxide.

Following this procedure we found that the phosphopeptides started to elute from the ion exchange column after approx. 42 ml of 0.05M sodium hydroxide was applied.

Another 25 ml of 0.05M sodium hydroxide was needed to elute all of the bound phosphopeptide. Thus the obtained eluate had a volume of 25 ml and although several column volumes of strong base had passed the column, the eluate had a nearly neutral pH-value of 8.5. The conductivity of the eluate was also surprisingly low at 2.5 mS/cm.

The eluate was freezedried without further treatment. 150 mg phosphopeptide of high purity was obtained.

Example 2
Isolation of Albumin Using an Amine Based Weak Anion Exchanger

A chromatographic column with an internal diameter of 1.6 cm was packed with a slurry of 12 ml DEAE-Sepharose Cl 6B (Pharmacia, Sweden). The column was first washed with 20 ml 1M hydrochloric acid followed by 20 ml 1M $K_2HPO_4$/HCl pH 6.8 and then 120 ml 0.01M $K_2HPO_4$/HCl pH 6.8.

20 ml bovine albumin, 50 mg/ml in 0.01M $K_2HPO_4$/HCl pH 6.8, was applied to the column, followed by washing with 20 ml of 0.01M $K_2HPO_4$/HCl pH 6.8. The content of albumin in the unbound fraction was determined by spectrophotometry.

The bound albumin was eluted from the column by application of a solution of 0.025M sodium hydroxide.

The eluate from the column was continuously monitored by a UV-monitor and collection of the eluted albumin in a stirred vessel began when the UV-monitor indicated the breakthrough of eluted albumin.

After complete elution the conductivity and pH were measured in the pooled eluate. The total amount of eluted albumin was determined by spectrophotometry.

In total 425 mg albumin was eluted, corresponding to 95% of what was initially bound. The total elution volume was 41 ml. The pH was 6.8 and the conductivity was 2.8 mS/cm, which is equivalent to a salt concentration of less than 30 mM sodium chloride. A conductivity of 3.0 mS/cm corresponds to 30 mM sodium chloride.

The results showed that the bound albumin was eluted in a solution low in salt contents and with a nearly neutral pH.

Example 3
Isolation of Bovine Gamma-Globulins Using A Carboxylic Based Weak Cation Exchanger A chromatographic column with an internal diameter of 1.6 cm was packed with a slurry of 12 ml CM-Sepharose CL 6B (Pharmacia, Sweden) having 120 micromoles of carboxylic acid groups per milliliter having 120 micromoles of carboxylic acid..groups per milliliter. The column was first washed with 20 ml 1M Sodium hydroxide followed by 20 ml 1M sodium acetate pH 5.0 and then 120 ml 0.01M sodium acetate pH 5.0.

20 ml bovine gamma-globulins, 10 mg/ml in 0.01M sodium acetate pH 5.0, was applied to the column, followed by washing with 40 ml 0.01M sodium acetate pH 5.0.

The bound gamma-globulin was eluted from the column by application of a solution of 0.050M hydrochloric acid.

The eluate from the column was continuously monitored by a UV-monitor and collection of the eluted gamma-globulin in a stirred vessel was commenced when the UV-monitor indicated the breakthrough of eluted gamma-globulin.

After elution the volume, conductivity and pH were measured in the pooled eluate. The total amount of eluted gamma-globulin was determined by spectrophotometry.

The result from this elution procedure was an eluate of 25 ml containing 130 mg gamma-globulin. The pH of the eluate was 3.9 and the conductivity was 4.7 mS/cm.

The results showed that the bound gamma-globulin was eluted in a solution low in salt contents and with a non-denaturing pH value.

Example 4
Isolation of Bovine Hemoglobin Using A Carboxylic Based Weak Cation Exchanger A chromatographic column with an internal diameter of 1.6 cm was packed with a slurry of 12 ml CM-Sepharose CL 6 B (Pharmacia, Sweden) having 120 micromoles of carboxylic acid groups per milliliter, having 120 micromoles of carboxylic acid groups per milliliter. The column was first washed with 20 ml 1M Sodium hydroxide followed by 20 ml 1M sodium acetate and then 120 ml 0.01M sodium acetate pH 5.0.

20 ml bovine hemoglobin, 50 mg/ml in 0.01M sodium acetate pH 5.0, was applied to the column, followed by washing with 80 ml 0.01M sodium acetate pH 5.0.

The bound hemoglobin was eluted from the column by application of a solution of 0.025M hydrochloric acid.

The eluate from the column was continuously monitored by a UV-monitor and collection of the eluted hemoglobin in a stirred vessel was commenced when the UV-monitor indicated the breakthrough of eluted hemoglobin.

After elution the volume, conductivity and pH were measured in the pooled eluate. The total amount of eluted hemoglobin was determined by spectrophotometry.

The result from this elution procedure was an eluate of 30 ml containing 650 mg hemoglobin. The pH of the eluate was 3.6 and the conductivity was 3.5 mS/cm.

The results showed that the bound hemoglobin was eluted in a solution low in salt contents and with a non-denaturing pH value.

Example 5
Isolation of Casein Phosphopeptides Using Fluid Bed Chromatography with Density Controlled Ion Exchange Particles Density controlled agarose based ion exchange particles were provided by Upfront Chromatography A/S, Copenhagen, Denmark (tradename "UFC-weak anion exchanger"). This density controlled ion exchanger contains 200 micromoles amino groups per ml sedimented matrix. The density of the ion exchange matrix is controlled by the incorporation of heavy glass particles in the polymer. The density of the matrix is approx. 1.3 g/ml.

One hundred millilitres of density controlled ion exchange particles were washed on a suction filter with 200 ml 1M hydrochloric acid followed by 2 λ 0.1M sodium chloride. The ion exchange matrix was then suspended in 200 ml 0.1M sodium chloride and transferred to a column consisting of a 5 cm inner diameter glass tube with a coarse filter in the bottom. There was no filter at the top of the column.

A 10% solution of sodium caseinate was hydrolyzed with trypsin followed by adjustment of pH to 4.6. The insoluble precipitates were not removed. This solution was diluted with one volume of 0.2M sodium chloride to obtain a final salt concentration of 0.1M.

500 ml of this milky solution was pumped into the column through the bottom port making the high density ion exchange matrix expand approx 2–3 times the sedimented volume. The milky solution was recirculated 5 times, whereafter the column was washed with 1 liter 0.1M sodium chloride. Hereby was all soluble and insoluble impurities from the sample washed out of the column, making elution from a packed bed possible.

Elution of the bound phosphopeptides was performed by application of 0.05M sodium hydroxide from the top of the column.

The eluate from the column was continuously monitored by a UV-monitor and collection of the eluted phosphopeptides in a stirred vessel was commenced when the UV-monitor indicated the breakthrough of eluted phosphopeptide.

After elution the volume, conductivity and pH were measured in the pooled eluate. The total amount of eluted phosphopeptide was determined by spectrophotometry and the purity was estimated by FPLC analysis.

The result from this procedure was an eluate of 250 ml containing 1650 mg phosphopeptide of high purity. The pH of the eluate was 8.3 and the conductivity was 3.5 mS/cm.

Example 6
Isolation of Casein Phosphopeptides Using An Acrylic Based Weak Anion Exchanger (a) Loading of 40 ml Solution of Casein Phosphopeptide An anion exchange for industrial use was synthesized by copolymerization of N-hydroxyacrylamide, bis-acrylamide and glycidoxymethacrylamide in an aqueous medium, followed by disintegration of the resulting polymer into small particles with a diameter between 200 and 500 micrometer. The polymer beads were then derivatized with ethylenediamine. The resulting anion exchanger contained approx. 250 micromoles amino groups per ml swollen beads and had a $pK_b$ value in the range from 4 to 10.

A chromatographic column with an internal diameter of 1.6 cm was packed with a slurry of 17 ml of the acrylic based anion exchanger. The column was first washed with 30 ml 1M hydrochloric acid followed by 200 ml 0.1M sodium chloride.

A 10% solution of sodium caseinate (Miprodan 30, MD Foods, Denmark) was hydrolyzed with trypsin (PTN 3.0, Type Special, Novo Nordisk, Denmark). The insoluble fraction was removed by adjustment of the pH to 4.6 followed by ultrafiltration.

The obtained solution (ultrafiltrate) containing the casein phosphopeptides was diluted with one volume 0.2M sodium chloride to obtain a final salt concentration of 0.1M.

40 ml of this solution was applied to the ion exchange column. The unbound fraction was washed out with a solution of 0.1M sodium chloride.

Elution of the bound phosphopeptides was performed by application of a solution of 0.05M sodium hydroxide.

Following this procedure we found that the phosphopeptides started to elute from the ion exchange column after approx. 45 ml of 0.05M sodium hydroxide was applied. Another 30 ml of 0.05M sodium hydroxide was needed to elute all of the bound phosphopeptide. Thus the obtained eluate had a volume of 30 ml and although several column volumes of strong base had passed the column, the eluate had a nearly neutral pH-value of 8.0. The conductivity of the eluate was 2.0 mS/cm.

The eluate was freezedried without further treatment. 200 mg phosphopeptide of high purity was obtained.

(b) Loading of 80 ml Solution of Casein Phosphopeptides

A chromatographic column with an internal diameter of 1.6 cm was packed with a slurry of 17 ml of the acrylic based anion exchanger mentioned under (a). The column was first washed with 30 ml 1M hydrochloric acid followed by 200 ml 0.1M sodium chloride.

A 10% solution of sodium caseinate (Miprodan 30, MD Foods, Denmark) was hydrolyzed with trypsin(PTN 3.0, Type Special, Novo Nordisk, Denmark). The insoluble fraction was removed by adjustment of the pH to 4.6 followed by ultrafiltration.

The obtained diafiltrate containing the casein phosphopeptides was diluted with one volume 0.2M sodium chloride to obtain a final salt concentration of 0.1M.

80 ml of this solution was applied to the ion exchange column. The unbound fraction was washed out with a solution of 0.1M sodium chloride.

Elution of the bound phosphopeptides was performed by application of a solution of 0.05M sodium hydroxide.

Following this procedure we found that the phosphopeptides started to elute from the ion exchange column after approx. 42 ml of 0.05M sodium hydroxide was applied. Another 30 ml of 0.05M sodium hydroxide was needed to elute all of the bound phosphopeptide. The eluate had a nearly neutral pH-value of 6.0. The conductivity of the eluate was 2.0 mS/cm. The eluate was freezedried without further treatment. 273 mg phosphopeptide of high purity was obtained.

(c) Loading of 2000 ml Solution of Casein Phosphopeptides

A chromatographic column with an internal diameter of 5.5 cm was packed with a slurry of 380 ml of the acrylic based anion exchanger mentioned under (a). The column was first washed with 0.5 $\lambda$ 1M hydrochloric acid followed by 5 $\lambda$ 0.1M sodium chloride.

A 10% solution of sodium caseinate (Miprodan 30, MD Foods, Denmark) was hydrolyzed with trypsin (PTN 3.0, Type Special, Novo Nordisk, Denmark). The insoluble fraction was removed by adjustment of the pH to 4.6 followed by ultrafiltration.

The obtained diafiltrate containing the casein phosphopeptides was diluted with one volume 0.2M sodium chloride to obtain a final salt concentration of 0.1M.

2000 ml of this solution was applied to the ion exchange column. The unbound fraction was washed out with a solution of 0.1M sodium chloride.

Elution of the bound phosphopeptides was performed by application of a solution of 0.05M sodium hydroxide.

Following this procedure we obtained 820 ml eluate. The eluate had a neutral pH-value of 7.0. The conductivity of the eluate was 2.2 mS/cm.

The eluate was freeze dried without further treatment. 7.5 g phosphopeptide of high purity was obtained.

(d) pH of Eluate Samples

A chromatographic column with an internal diameter of 11.3 cm was packed with a slurry of 1.45 $\lambda$ of the acrylic based anion exchanger mentioned under (a). The column was first washed with 1.5 $\lambda$ 1M hydrochloric acid followed by 15 $\lambda$ 0.1M sodium chloride.

A 10% solution of sodium caseinate (Miprodan 30, MD Foods, Denmark) was hydrolyzed with trypsin (PTN 3.0, Type Special, Novo Nordisk, Denmark) at pH 8.0, 50 °/C. for two hours. The enzyme to substrate ratio was 1:200 (w/w). The insoluble fraction was removed by diafiltration after adjustment of the pH to 4.5.

The resulting diafiltrate of 3.6% protein (Nitrogen Analyzer macro N, Foss Heraeus, Germany) was diluted with one volume 0.2M sodium chloride to obtain a final salt concentration of 0.1M. 8 $\lambda$ of this solution was applied to the ion exchange column and the unbound fraction was washed out with 6 $\lambda$ 0.1M sodium chloride.

Elution of the bound phosphopeptides was performed by application of a solution of 0.05M sodium hydroxide. The phosphopeptides began to elute from the ion exchange column after approximately 2.8 $\lambda$ of 0.05M sodium hydroxide was applied. Another 2.5 $\lambda$ of 0.05M sodium hydroxide was needed to elute all of the bound phosphopeptide.

The eluate had 29.0 grams of casein phosphopeptides in a volume of 2.5 $\lambda$, a nearly neutral pH value of 8.30, and a conductivity of the eluate of 2.3 mS/cm.

The experiment was repeated with the only alternative being that the column was eluted with 0.6M sodium hydroxide instead of 0.05M sodium hydroxide.

In this case 31.0 grams of casein phosphopeptide was obtained in a volume of 1.8 λ. the pH was 12.0 and the conductivity was 53.4 mS/cm.

During elution samples of 10 ml eluate were collected and the pH in these was measured in both experiments.

Figure 3:
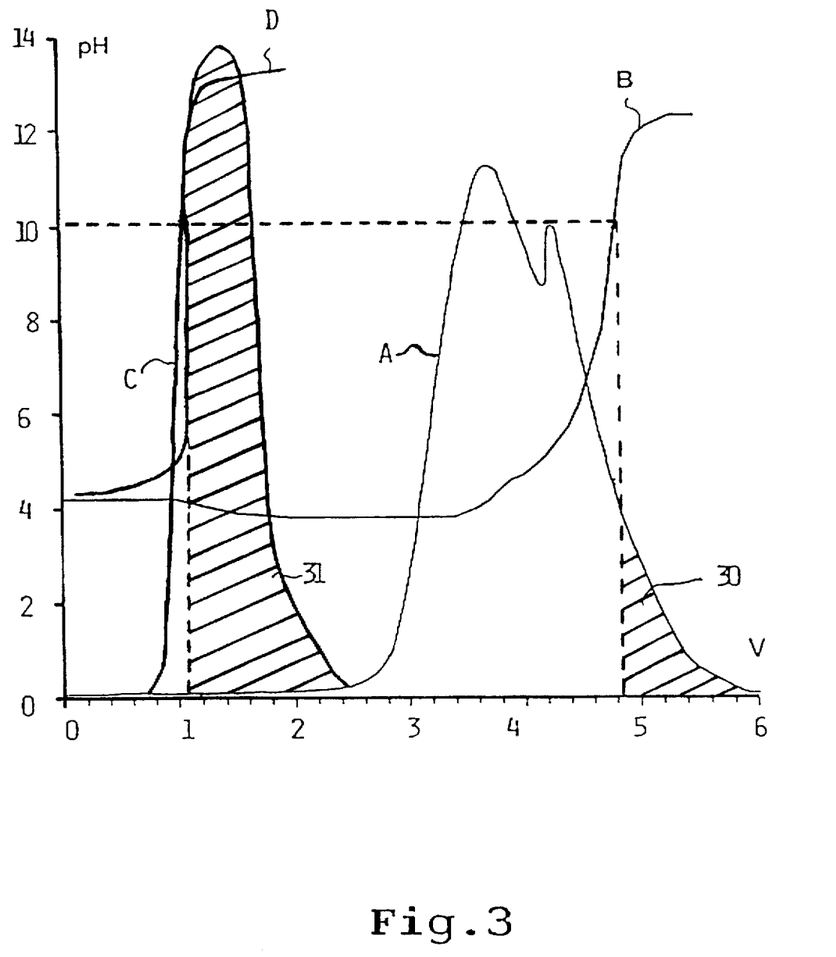
FIG. 3 shows illustrations of the elution of casein phosphopeptides (A, C) and of the concurrent pH-values of the eluates (B, D) for sodium hydroxide concentrations of 0.05M and 0.6M, respectively, in the eluant.

In FIG. 3 the elution of casein phosphopeptides is illustrated for the absorbance at 280 nm. curve A (0.05M NaOH) and C (0.6MNaOH). versus the elution volume together with the concurrent pH of 10 ml samples. curve B (0.05MNaOH) and D (0.6MNaOH).

As shown in FIG. 3 the fraction of casein phosphopeptides exposed to a pH value larger than 10 is much larger for the 0.6MNaOH eluant concentration (31) than for the 0.05MNaOH eluant concentration (30).

Example 7
Isolation of Casein Phosphopeptides Using An Agarose Based Weak Anion Exchanger (a) Addition of NaCl to A Final Concentration of 0.05M of the Diafiltrate A chromatographic column with an internal diameter of 25 cm was packed with a slurry of 36 λ of weak anion exchanger (PA Agarose. Kem-En-Tec. Denmark) with 200 millimoles exchanging groups per gram and a $pK_b$ from 4 to 10. The column was first washed with 23 λ 1M hydrochloric acid followed by 135 λ of 0.05M sodium chloride.

A 10% solution of sodium caseinate (Miprodan 30. MD Foods. Denmark) was hydrolyzed with trypsin (PTN 3.0. Type Special. Novo Nordisk. Denmark) at pH 8.0, 50 ° C. for two hours. The enzyme to substrate ratio was 1:200 (w/w). The insoluble fraction was removed by diafiltration after adjustment of the pH to 4.5.

The resulting diafiltrate of 3.6% protein (Nitrogen Analyzer macro N. Foss Heraeus, Germany) was added sodium chloride to obtain a final concentration of 0.05M. 180 λ of this solution was applied to the ion exchange column and the unbound fraction was washed out with a solution of 0.05M sodium chloride.

Elution of the bound phosphopeptides was performed by application of a solution of 0.05M sodium hydroxide. The phosphopeptides started to elute from the ion exchange column after 83 λ of 0.05M sodium hydroxide was applied. Another 86 λ of 0.05M sodium hydroxide was needed to elute all of the bound phosphopeptide.

The eluate had a neutral pH value of 7.00, a conductivity of 2.4 mS/cm and a protein concentration of 1.05%. 900 g high purity phosphopeptides were obtained. Purity was determined by the Purity Test described above.

(b) No Addition of NaCl to the Diafiltrate

The chromatographic column and ion exchanger. mentioned under (a), were used for isolation of phosphopeptides from the diafiltrate of the same lot as obtained under (a).

The ion exchanger was first washed with hydrochloric acid as described. Following this step, the ion exchanger was washed with water. The diafiltrate was not added sodium chloride before it was applied to the ion exchanger.

The unbound fraction was washed out with water and the elution of phosphopeptides was performed as described under (a). The similar amount of phosphopeptides and purity of these was obtained as under (a).

(c) Elution with 0.1M NaOH

The chromatographic column and ion exchanger. mentioned under (a), was used for isolation of phosphopeptides from the diafiltrate of the same lot as obtained under (a).

The unbound fraction was washed out with 0.05M sodium chloride and the elution of phosphopeptides was performed with 0.1M sodium hydroxide.

The phosphopeptides started to elute from the ion exchange column after 74 λ of 0.1M sodium hydroxide was applied.

Another 55 λ of 0.1M sodium hydroxide was needed to elute all of the bound phosphopeptides.

The eluate had a nearly neutral pH value of 8.94. a conductivity of 4.18 mS/cm and a protein concentration of 1.71%. 940 g of phosphopeptide of high purity. determined by the Purity Test described above. was obtained.

(d) No Regeneration of the Ion Exchanger

A chromatographic column with an internal diameter of 25 cm was packed with a slurry of 48 λ of the agarose based weak anion exchanger. mentioned under (a). The ion exchanger was first washed with 158 λ of 0.05M sodium chloride omitting regeneration of the ion exchanger with hydrochloric acid.

A diafiltrate was prepared as described under (a) and this was added sodium chloride to obtain a final concentration of 0.05M. 250 λ of this solution was applied to the ion exchange column. The unbound fraction was washed out with a solution of 0.05M sodium chloride.

Elution of the bound phosphopeptides was performed by application of a solution of 0.1M sodium hydroxide. The phosphopeptides began to elute from the ion exchange column after 63 λ of 0.1M sodium hydroxide was applied. Another 60 λ of 0.1M sodium hydroxide was needed to elutei all of the bound phosphopeptide.

The eluate had a nearly neutral pH value of 6.82. a conductivity of 4.82 mS/cm and a protein concentration of 1.90%. 1150 g of high purity phosphopeptide was obtained, as determined by the Purity Test described above.

Example 8
The Effect of Eluant Concentration

A chromatographic column with an internal diameter of 1 cm was packed with a slurry of 22 ml of weak anion exchanger, described in Example 7(a). The column was first washed with 3 λ of 1M hydrochloric acid followed by water.

A diafiltrate was prepared as described in Example 7(a). 110 ml of this was applied to the ion exchanger followed by wash out of the unbound fraction using water.

Elution of the bound phosphopeptides was performed by application of a sodium hydroxide solution. The eluted phosphopeptides were pooled. The volume, pH value and the conductivity of the pooled phosphopeptides were measured.

A number of identical assays were performed where only the eluant concentration was varied. The results are shown in Table 1.

For comparison, the similar parameters were measured for the salt elution using 0.5M KCl and 1M NaCl according to prior art are shown in Table 2.

TABLE 1

| Eluant: NaOH | | Pool Phosphopeptides | | |
|---|---|---|---|---|
| C (mol/l) | κ (mS/cm) | V (ml) | pH | κ (mS/cm) |
| 0.05 | 11.12 | 28.5 | 7.23 | 3.00 |
| 0.1 | 20.2 | 23.8 | 8.75 | 6.13 |
| 0.2 | 40.1 | 16.2 | 9.89 | 10.52 |
| 0.4 | 81.3 | 15.1 | 11.6 | 14.20 |
| 0.6 | 118.8 | 21.6 | 12.14 | 55.30 |

TABLE 2

| | Pool Phosphopeptides | | | |
|---|---|---|---|---|
| Eluant | κ (mS/cm) | V (ml) | pH | κ (mS/cm) |
| 0.5 M KCl | 56.3 | 31.26 | 10.27 | 50.4 |
| 1 M NaCl | 79.5 | 24.0 | 5.50 | 58.7 |

Legends for Tables 1 and 2:
C: Concentration of eluant
κ: Conductivity of the eluant or pooled eluate, respectively
V: Volume of the pooled eluate
pH: pH of the pooled eluate As the conductivity, κ, of a solution is dependent on the nature of the present ions and the concentration of these, the measured conductivity of a solution is the sum of the concentration of all ions present in the solution.

By elution with the strong base sodium hydroxide of low concentration, 0.05M, almost no excess ions were obtained in the pool of phosphopeptide resulting in a conductivity of 3.00 (mS/cm).

By increasing the sodium hydroxide concentration of the eluant the conductivity of the resultant pool of phosphopeptides was increased (Table 1). This increase in conductivity is caused by the increasing concentration of sodium hydroxide in the eluate. Because of the high concentration of sodium hydroxide in the eluant, e.g. 0.6 (mol/λ), excess sodium hydroxide is eluted together with the phosphopeptides. This excess of sodium hydroxide is indicated by the high pH value 12.14 of the eluate pool.

As shown in Table 2 using a salt solution as the eluant results in nearly neutral pH of the eluted phosphopeptide; and an extremely high conductivity, indicating a high concentration of salt in the eluate which is a major drawback of elution with salt eluants.

In conclusion, in order to elute phosphopeptides and obtain a phosphopeptide pool containing a minimum of free ions, the concentration of the eluting base must be low. In this series of experiments this was obtained for a sodium hydroxide concentration from 0.05M to 0.2M and to some extent at 0.4M.

In contrast to this, when the phosphopeptides are eluted with a base of high concentration, such as 0.6M sodium hydroxide or above, the pH value of the resultant pool of phosphopeptides is very high, 12.14 or above.

As a consequence, in order to obtain a pool of phosphopeptides with a low content of free ions and a nearly neutral pH, the concentration of eluting base must be equal to or less than the concentration of the ion exchanging groups of the ion exchange material.

Example 9
Degree of Phosphorylation, Purity and Yield of the Isolated Casein Phosphopeptides The degree of phosphorylation, purity and yield quality of casein phosphopeptides isolated according to the invention was compared with those of a casein phosphopeptide product isolated according to prior art.

(a) Degree of Phosphorylation

Several lots, A–E, of casein phosphopeptides were isolated as described in Example 7(d) and casein phosphopeptides, CPP III, were obtained from Meiji Seika Kaishe Inc., Japan.

The protein concentration was calculated as protein (%)= N(%)×6.38, where N(%) (nitrogen) was determined according to the method by Dumas using a Nitrogen Analyzer macro N supplied by Foss Heraeus, Germany; serin (%) was determined according to the reference method AACC 07-01 of the American Association of Cereal Chemists; and P(%) (phosphate) was determined by the method of ICP Mineral Analysis described in Fres. Z. Anal. Chem. 1985, p. 37.

The results are shown in Tables 3 and 4.

TABLE 3

| Product | Protein (%) | Serin (%) | P (%) | N (%) |
|---|---|---|---|---|
| Lot No. A | 71.7 | 11.2 | 3.61 | 11.3 |
| Lot No. B | 72.3 | 11.4 | 3.67 | 11.3 |
| Lot No. C | 72.9 | 11.7 | 3.71 | 11.4 |
| Lot No. D | 71.6 | 12.0 | 3.69 | 11.2 |
| Lot No. E | 72.49 | 10.5 | 3.15 | 11.4 |
| CPP III | 79.7 | 9.78 | 2.75 | 12.5 |

TABLE 4

| Product | N/P (mol/mol) | N/Serin (mol/mol) | Serin/P (mol/mol) |
|---|---|---|---|
| Lot No. A | 6.92 | 7.56 | 0.92 |
| Lot No. B | 6.81 | 7.43 | 0.92 |
| Lot No. C | 6.79 | 7.30 | 0.93 |
| Lot No. D | 6.71 | 7.00 | 0.84 |
| Lot No. E | 8.00 | 8.11 | 0.98 |
| CPP III | 10.05 | 9.58 | 1.06 |

Compared to the prior art CPP III, the casein phosphopeptides isolated according to the invention exhibit a higher phosphate content indicating a higher yield of phosphopeptides. Further, the nitrogen content is low corresponding to the lower protein content.

In Table 4 the ratios N/P, N/Serin and Serin P are shown. The N/P and N/Serin ratios were calculated as follows:

$$N/P \text{ (mol/mol)} = \frac{N(g)/14.01 \text{ (g/mol)}}{P(g)/30.97 \text{ (g/mol)}}$$

$$N/Serin \text{ (mol/mol)} = \frac{N(g)/14.01 \text{ (g/mol)}}{Serin(g)/105 \text{ (g/mol)}}$$

A low N/P-ratio indicates that the phosphopeptides are highly phosphorylated. A low N/serin-ratio indicates that the phosphopeptides have a high serin content. The serin/P-ratio close to one indicates that all serin residues are phosphorylated.

In the isolated casein phosphopeptides obtained according to the invention, lot nos. A–E, there are 7-8 moles nitrogen per mole of serin and phosphate. As the serin/phosphate ratio is close to and even less than 1, it can be concluded that all of the serine residues are phosphorylated.

Further, the isolated casein phosphopeptides obtained according to the invention has a 5.1 fold increase in the phosphor content as opposed to the starting material, caseinate. Whereas the product produced according to prior art, CPP III, only shows a 3.9 increase in the phosphor content.

In conclusion, the casein phosphopeptides obtained according to the invention are highly phosphorylated, the product contains predominantly phosphorylated peptides and the overall yield of phosphopeptides from caseinate is 10-15 (w/w)%.

(b) Purity of Casein Phosphopeptides

The purity of casein phosphopeptides, CPP, isolated according to the present invention (FIG. 4B), were compared to the purity of phosphopeptides, CPP III, obtained from Meiji Seika Kaishe Inc., Japan (FIG. 4A) by means of the Purity Test described above.

Figure 4A:
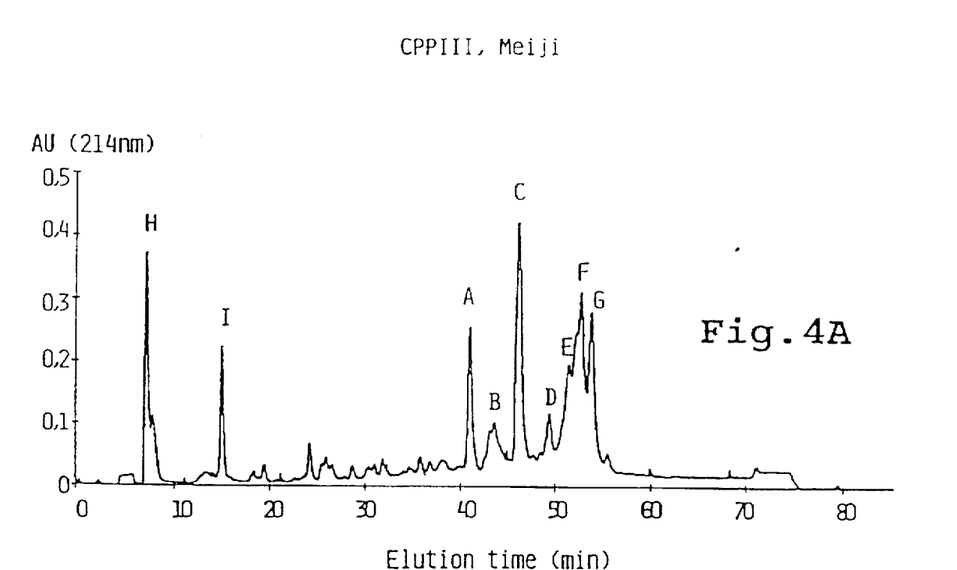
FIGS. 4A and 4B show analytical ion exchange chromatograms of prior art, casein phosphopeptides obtained from Meiji (4A) and casein phosphopeptides isolated by the method according to the invention (4B)
Figure 4B:
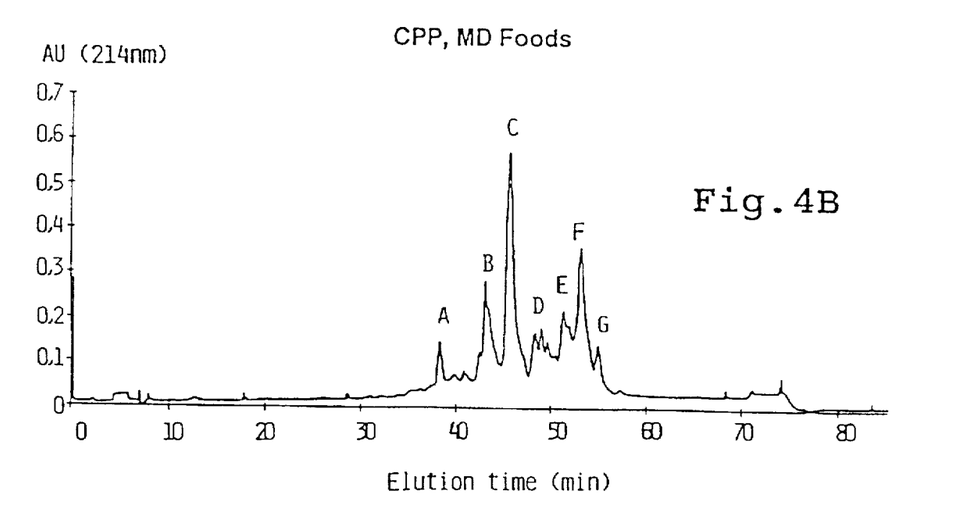

In FIG. 4B the components A–G of the CPP obtained according to the invention can also be found in FIG. 4A at approximately the same elution times. But in addition, the CPP III obtained according to a prior art method exhibits impurity, especially components H and I (FIG. 4A).

Consequently, the intensities of the peaks for the components A–G, i.e. the fraction of corresponding phosphopeptides, is larger for the CPP obtained according to the invention than for the prior art CPP III product.

Also, the purities of the corresponding dephosphorylated phosphopeptides dCPP (FIG. 5B) and dCPP III (FIG. 5A) were compared.

Figure 5A:
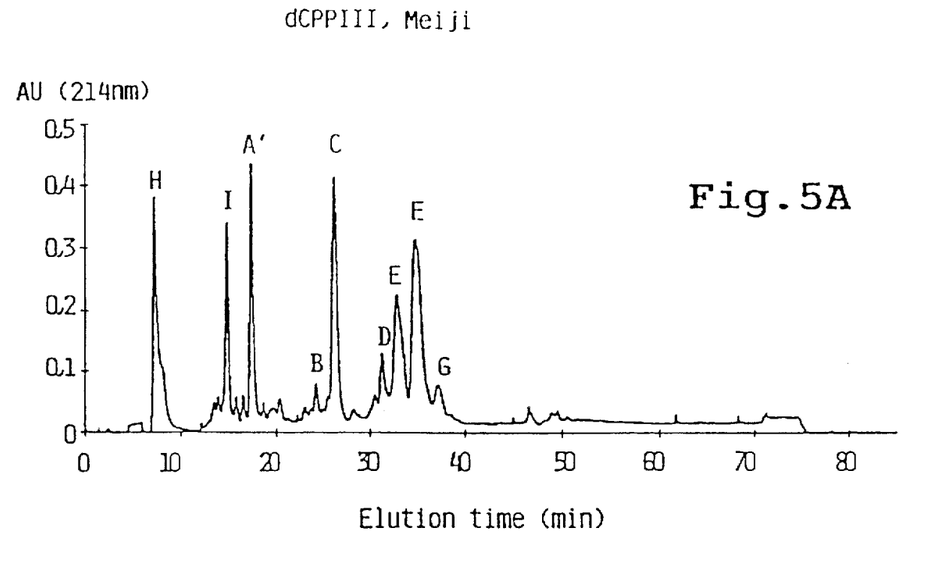
FIGS. 5A and 5B show analytical, ion exchange chromatograms of the dephosphorylated prior art casein phosphopeptides obtained by dephosphorylation of the casein phosphopeptides obtained from Meiji (5A) and the dephosphorylated casein phosphopeptides isolated by the method according to the invention (5B).
Figure 5B:
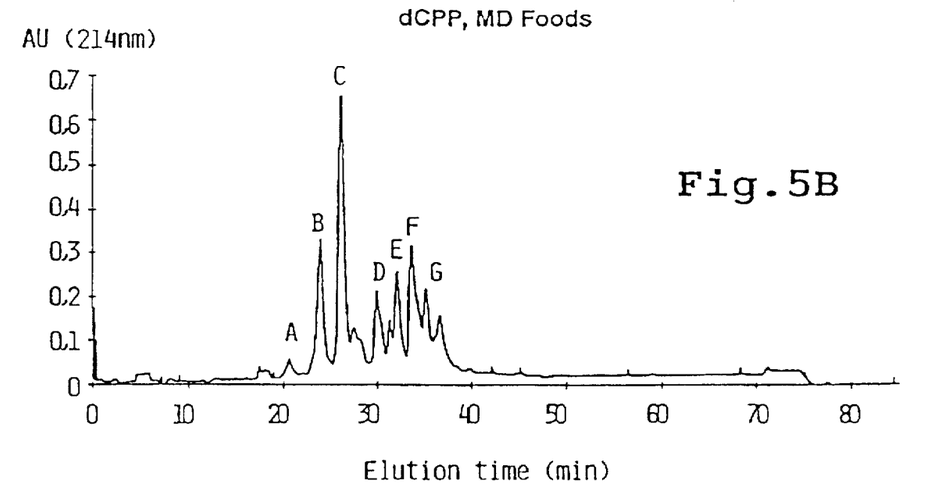

Firstly, by comparison of FIG. 4B and FIG. 5B, it can be seen that all the components A–G of the CPP obtained according to the invention are shifted to shorter elution times which indicates that the isolated phosphopeptides consists of only phosphopeptides which can be dephosphorylated.

Secondly, by comparison of FIG. 4A and FIG. 5A, it can be seen that all the components A–G are shifted to shorter elution times which indicates that these components are phosphopeptides.

In FIG. 5A it is seen that the component A' has been shifted more than the components B–G, and that the components H and I are not shifted at all which indicates that at least the components H and I are not phosphopeptides which can become dephosphorylated.

In conclusion, the purity of the CPP isolated according to the present invention is better than the purity of the CPP III product obtained by a prior art method.

(c) Yield of Casein Phosphopeptides

The yield of casein phosphopeptides isolated from the starting material caseinate according to the invention was compared with the yield of casein phosphopeptides isolated according to the prior art method by Juillerat et al., Journal of Dairy Research, Vol. 56, 603–611, 1989. The yield is calculated as $$\text{yield} = \frac{\text{weight of casein phosphopeptides (kg)}}{\text{weight of caseinate (kg)}} \times 100\%$$

The results are shown in Table 5.

The yield of casein phosphopeptides isolated according to the invention was in the range of 13–16% of the weight of the starting material, caseinate, which was significantly higher than the yields obtained by the prior art method.

TABLE 5

| Reference | Caseinate (kg) | CPP (kg) | Yield (%) |
|---|---|---|---|
| Example 7 (d) | 13.7 | 2.2 | 16.1 |
| A (a) | 200 | 27.2 | 13.6 |
| Prior art (b) | 1 | ≈0.08 | ≈8.0 |

(a) Large scale isolation of casein phosphopeptides starting with the hydrolysation of 200 kg sodium caseinate.
(b) Casein phosphopeptides isolated by the prior art method of Juillerat et al., ibid. The phosphopeptides contained impurities in form of non-phosphorylated peptides. The amount of impurities was estimated to be ⅓ of the total 0.120 kg product, i.e. 0.04 kg of impurities.

Example 10
Production of Calcium-CPP

Casein phosphopeptides produced according to the invention was used to produce casein phosphopeptide bound calcium, Ca-CPP.

Casein phosphopeptides were eluted from an anion exchanger as described in Example 7(a). Half of the pool of peptidies designated Na-CPP was dried and analysed. The remaining half of the pool of casein phosphopeptides was added approx. 100 g calcium chloride, $CaCl_2$ per kilo casein phosphopeptides. The pool was concentrated using reversed osmosis, and it was washed repeatedly by addition of deionized water in order to wash out-excess ions and non-peptide bound ions with the permeate. The obtained concentrate designated Ca-CPP was then dried and analysed.

The results are shown in Table 6.

The concentration of calcium in Ca-CPP was significantly larger than in Na-CPP and the concentration of sodium was significantly lower than Na-CPP. This indicates that the peptide bound sodium can be exchanged with calcium.

TABLE 6

| Product | Na-CPP | Ca-CPP |
|---|---|---|
| Calcium % | 0.32 | 6.50 |
| Sodium % | 7.00 | 1.43 |

We claim:

1. A method of isolating a biomolecule consisting of a protein or a peptide from a medium containing biomolecules by ion exchange wherein an eluate contains a low salt concentration so that a desalination treatment can be avoided, which method comprises the steps of:
   a) packing a column with an ion exchange material consisting of a material having ion exchanging groups which can be transformed from a charged form to an uncharged form;
   b) applying the medium containing biomolecules to the ion exchange material;
   c) binding said biomolecules to be isolated to the ion exchange material; and
   d) eluting the bound biomolecules from the ion exchange material by an eluant comprising a charge neutralizing acid or base which transforms the ion exchanging groups from the charged form to the uncharged form; wherein that the charge neutralizing acid or base has a concentration in the eluant which is up to twice the concentration of the ion exchanging groups of the ion exchange material; and said ion exchange material is in a packed, hydrated state.

2. A method according to claim 1, wherein a salt having a concentration in the range from about 0.1 normal to about 0.3 normal is added to the medium containing biomolecules prior to the step of applying the medium to the ion exchange material, or to a washing solution used during a step of washing out unbound biomolecules, or both.

3. A method according to claim 1, wherein the biomolecule is selected from proteins or peptides contained in biological materials selected from the group consisting of food, feed, biproducts and waste produced in the production of foods and feeds.

4. A method according to claim 1, wherein the biomolecule is a protein selected from the group consisting of enzymes, albumin, hemoglobin, and immunoglobulin from human, porcine or bovine blood; a milk protein selected from the group consisting of immunoglobulin, lactoferrin, lactoglobulin, and lactoperoxidase from milk or whey; or an egg white protein.

5. A method according to claim 1, wherein the biomolecule is a peptide and is a phosphopeptide from casein.

6. A method according to claim 1, wherein the applying and eluting steps are carried out, wholly or partially in a fluidized bed.

7. A method according to claim 1, wherein the ion exchange material is in the form of particles having controlled density.

8. A method according to claim 1, further comprising a step of equilibrating the ion exchange material prior to said applying step.

9. A method according to claim 1, wherein the concentration of the ion exchanging groups of the ion exchange material is in the range from about 50 to about 500 microequivalents per milliliter of packed, hydrated ion exchange material.

10. A method according to claim 9, wherein the concentration of the ion exchanging groups of the ion exchange material is in the range from about 100 to about 300 microequivalents per milliliter of packed, hydrated ion exchange material.

11. A method according to claim 1, further comprising a step of washing out unbound biomolecules after said binding step and before eluting the bound biomolecules.

12. A method according to claim 11, wherein the step of applying the medium containing biomolecules, the step of washing out unbound biomolecules, or both, are carried out in a batch process.

13. A method of using a biomolecule consisting of a protein or a peptide isolated by a method according to claim 1 for the production of a food, a feed, a health care product, a cosmetic, or a pharmaceutical.

14. A method according to claim 13, wherein the isolated biomolecule is casein phosphopeptide in the form of calcium casein phosphopeptide.

15. A method according to claim 1, wherein the ion exchange material is an anion exchanger, and the charge neutralizing acid or base is a base having a $pK_b$ less than the $pK_b$ of the anion exchanger.

16. A method according to claimed 15, wherein the charge neutralizing acid or base is a base having a $pK_b$ more than 2 $pK_b$ units less than the $pk_b$ of the anion exchanger.

17. A method according to claim 15, wherein the charge neutralizing acid or base is a base having a $pK_b$ less than 1.

18. A method according to claim 1, wherein the ion exchange material is a cation exchanger, and the charge neutralizing acid or base is an acid having a $pK_a$ less than the $pK_a$ of the cation exchanger.

19. A method according to claim 18, wherein the charge neutralizing acid or base is an acid having a $pK_a$ more than 2 $pk_a$ units less than the $pK_a$ of the cation exchanger.

20. A method according to claim 18, wherein the charge neutralizing acid or base is an acid having a $pK_a$ less than 1.

21. A method according to claim 1, wherein the concentration of the charge neutralizing acid or base in the eluant is in the range from about 0.1% to 200% of the concentration of the ion exchanging groups of the packed, hydrated ion exchange material.

22. A method according to claim 21, wherein, the concentration of the charge neutralizing acid or base in the eluant is in the range from about 1% to 100% of the concentration of the ion exchanging groups of the packed, hydrated ion exchange material.

23. A method according to claim 22, wherein the concentration of the charge neutralizing acid or base in the eluant is in the range from about 5% to 75% of the concentration of the ion exchanging groups of the packed, hydrated ion exchange material.

24. A method according to claim 23, wherein the concentration of the charge neutralizing acid or base in the eluant is in the range from about 5% to 50% of the concentration of the ion exchanging groups of the packed, hydrated ion exchange material.

25. A method according to claim 24, wherein the concentration of the charge neutralizing acid or base in the eluant is in the range from about 5% to 35% of the concentration of the ion exchanging groups of the packed, hydrated ion exchange material.

26. A method according to claim 1, wherein the biomolecule is a phosphopeptide; and a) the ion exchange material is an anion exchanger having a $pK_b$ in the range from about 3 to about 10;

b) the eluant is an aqueous solution of a base having a pH larger than 4, said base having a $pK_b$ value less than 5; and c) the base has a concentration less than 0.4N.

27. A method according to claim 26, wherein the medium has a pH in the range from about 3.5 to about 5.0 and contains about 0.1M sodium chloride.

28. A method according to claim 26, wherein the base is selected from the group consisting of sodium hydroxide, calcium hydroxide, and ammonium hydroxide.

29. A method according to claim 26, further including an equilibration step of washing the ion exchange material with a solution containing sodium chloride.

30. A method according to claim 26, wherein said base has a $pK_b$ value less than 3.

31. A method according to claim 30, wherein said base has a $pK_b$ less than 1.

32. A method according to claim 26, further comprising a step of washing out unbound biomolecules after said binding step and before eluting the bound biomolecules with a washing solution.

33. A method according to claim 32, wherein to the medium, the washing solution or both, there is added about 0.1M sodium chloride.

34. A method according to claim 32, wherein the washing solution contains about 0.1M sodium chloride.

35. A method according to claim 32, wherein the washing solution consists of pure water.

* * * * *